United States Patent [19]
Dooley et al.

[11] 3,938,440
[45] Feb. 17, 1976

[54] MIXED PROPELLANT CHARGE

[75] Inventors: James K. Dooley; Ralph L. Cook, both of Tallahassee, Fla.

[73] Assignee: Olin Corporation, New Haven, Conn.

[22] Filed: Mar. 14, 1974

[21] Appl. No.: 450,961

Related U.S. Application Data

[63] Continuation of Ser. No. 324,699, Jan. 18, 1973, abandoned.

[52] U.S. Cl. .................. 102/38; 102/100; 149/2
[51] Int. Cl.² ............................................ F42B 5/16
[58] Field of Search ............ 102/38, 40, 43, DIG. 1, 102/99, 100, 101, 102, 103, 104; 149/2, 21

[56] References Cited
UNITED STATES PATENTS

| | | | |
|---|---|---|---|
| 389,496 | 9/1888 | Brown | 102/40 |
| 1,018,312 | 2/1912 | Gherassimoff | 102/101 UX |
| 1,709,868 | 3/1929 | O'Neil | 149/21 |
| 2,072,671 | 3/1937 | Foulke | 102/38 X |
| 2,124,201 | 7/1938 | Lewis et al. | 102/99 X |
| 2,341,310 | 2/1944 | Calhoun et al. | 102/38 |
| 3,377,955 | 4/1968 | Hodgson | 102/102 |
| 3,706,278 | 12/1972 | Stiefel | 102/38 |

*Primary Examiner*—Samuel Feinberg
*Assistant Examiner*—Harold Tudor
*Attorney, Agent, or Firm*—Donald R. Motsko; William W. Jones

[57] ABSTRACT

A propellant charge comprising a matrix of granular propellant having interspersed therethrough compacted molded bodies of propellant. The density of the granular propellant is less than the density of the molded propellant bodies. The use of the mixed propellant charge enables a cartridge case of given dimensions to be loaded with a greater weight of propellant thereby enabling the achievement of greater projectile velocities in any given gun-ammunition system.

8 Claims, 4 Drawing Figures

MIXED PROPELLANT CHARGE

This is a continuation of application Ser. No. 324,699 filed Jan. 18, 1973 now abandoned.

This invention relates to a propellant charge having a matrix of a granular propellant in which there are interspersed compacted high density molded bodies of propellant material, and to a cartridge utilizing such a propellant charge.

In any given gun-ammunition system there are certain fixed factors and certain variable factors. For a particular caliber system, the fixed factors usually arise from the gun: such as barrel length and diameter, chamber configuration and volume. The variable factors are usually associated with the ammunition, projectile weight and propellant, but there are certain fixed variables also involved, specifically the cartridge case must be compatible with the chamber configuration, thus fixing a specific volume for propellant and projectile. The projectile must conform to a specific diameter, thereby changing weight by either a length or mass variation. It is apparent that lighter weight projectiles have the potential for nigher velocities in any given system. However, after selection of a given projectile with specific dimensions, the propellant volume in the case, behind the projectile, becomes also fixed, leaving only the propellant as a variable.

In the firing of such a gun-ammunition system, an additional limitation of maximum pressure is arbitrarily assigned to insure against malfunction of or damage to the gun mechanism. The primary object in selecting the proper propellant is to obtain the maximum projectile velocity while not exceeding the pressure limit.

In view of the foregoing, it is apparent that, for a particular established gun-ammunition system, the propellant charge in the round of ammunition is the variable consituent which can be most readily modified to change ballistics of the system without requiring re-working of the entire system. Vast amounts of time and effort have been expended in the past toward finding a solution to the problem of obtaining maximum velocity of a projectile through modification of the propellant charge used to propel the projectile.

The basic propellant used in modern small arms ammunition is smokeless powder. A great variety of smokeless powders have been produced for use as propellants for small arms ammunition, the various smokeless powders displaying different burning rates, different physical characteristics, shapes, and the like. The efficiency of a particular smokeless powder as a propellant for a particular system with respect to velocity can be measured by plotting its pressure/time curve, with the area under the curve being proportional in general to the velocity achieved by combustion of the propellant assuming bore resistances and heat losses are equivalent. An ideal smokeless powder propellant would produce a pressure/time curve which would quickly rise to its peak pressure, remain at the peak pressure for substantially the entire burning time, and then quickly fall back to zero with adiabatic expansion of combustion gases at the end of the burning time so as to maximize the area under the curve, thus maximizing the velocity. In fact, however, smokeless powders, when burned, produce a pressure/time curve which rises rather gradually to peak pressure, remains at peak pressure a relatively short time period, and then gradually drops back toward zero with adiabatic expansion of the combustion gases produced.

For any given propellant charge in a predetermined gunammunition system, there is a maximum potential velocity which could be imparted to a projectile, were the propellant charge functioning in this ideal manner. This maximum potential velocity is, at present, not attainable in practice, and a system can be said to be performing quite well where 85–90 percent of the maximum potential velocity is achieved. Maximum potential velocity for any given propellant can be plotted as a function of pressure for any given charge weight in any given system, and can also be plotted as a function of charge weight for any given pressure in a given system. In both cases, maximum potential velocity increases as pressure and charge weight increase.

Our solution to the problem of providing increased projectile velocity within any given gun-ammunition system is directed toward increasing the weight of the propellant charge which can be packed into a given volume, e.g. increasing the full case propellant charge weight. Conventional granular smokeless powder propellants have a packing density of no greater than about 1.00 gm./cc. Methods have recently been developed by which conventional granular smokeless powder propellants can be compacted into coherant bodies having a density of about 1.40 gm./cc. We have discovered that pellets of compacted smokeless powder can be mixed with granular smokeless powder propellant to provide a propellant mixture having a density of greater than 1.00 gm./cc. but less than 1.40 gms./cc. The size of the molded, compacted pellets should preferably be small compared to the dimensions of the cartridge case propellant chamber to provide maximum ease of loading the pellets into the casing, but should be large compared to the individual propellant granules of the granular constituent of the propellant mixture. The smokeless powder from which the molded pellets are made can be the same or a different formulation from the smokeless powder which forms the granular constituent of the mixed propellant of this invention.

As noted above, conventional granular smokeless powders can be said to be performing quite well if able to produce 85–90 percent of the maximum possible projectile velocity. Tests have shown, surprisingly, that the mixed propellant charge of this invention will also produce 85–90 percent of the maximum possible projectile velocity. Thus, due to the increased density of the mixed propellant charge as compared to a purely granular propellant charge, the mixed propellant charge will produce a higher projectile velocity in a given gun-ammunition system because a greater weight of propellant can be packed into the ammunition casing. It is hypothesized that the surprisingly favorable burning characteristics of the mixed propellant charge is the result of a delay in the ignition of the molded pellets, which once ignited, disintegrate and burn in the same fashion as the granular propellant. By way of demonstrating the increased propellant weight possible with the mixed propellant charge of this invention, a 30 mm WECOM cartridge cartridge was loaded solely with granular smokeless powder and was found to hold a full charge of 655 grains. The same cartridge was then loaded with a mixture of molded propellant pellets of the same propellant and approximately 0.30 in. × 0.20 in. × 0.15 in., and the granular propellant and was found to hold a full charge of approximately 800 grains.

It is, therefore, an object of this invention to provide a smokeless powder propellant mixture which will produce increased projectile velocity in any given gun-ammunition system as compared to a purely granular propellant charge in the same gun-ammunition system.

It is another object of the invention to provide a propellant charge which will provide increased projectile velocity without undersirably increasing chamber pressure.

It is a further object to provide a propellant mixture of the character described which includes high density molded propellant pellets dispersed in a matrix of granular propellant.

These and other objects and advantages of the invention will become more readily apparent from the following detailed description of a preferred embodiment of the invention when taken in conjunction with the accompanying drawings, in which.

Figures 1, 2:
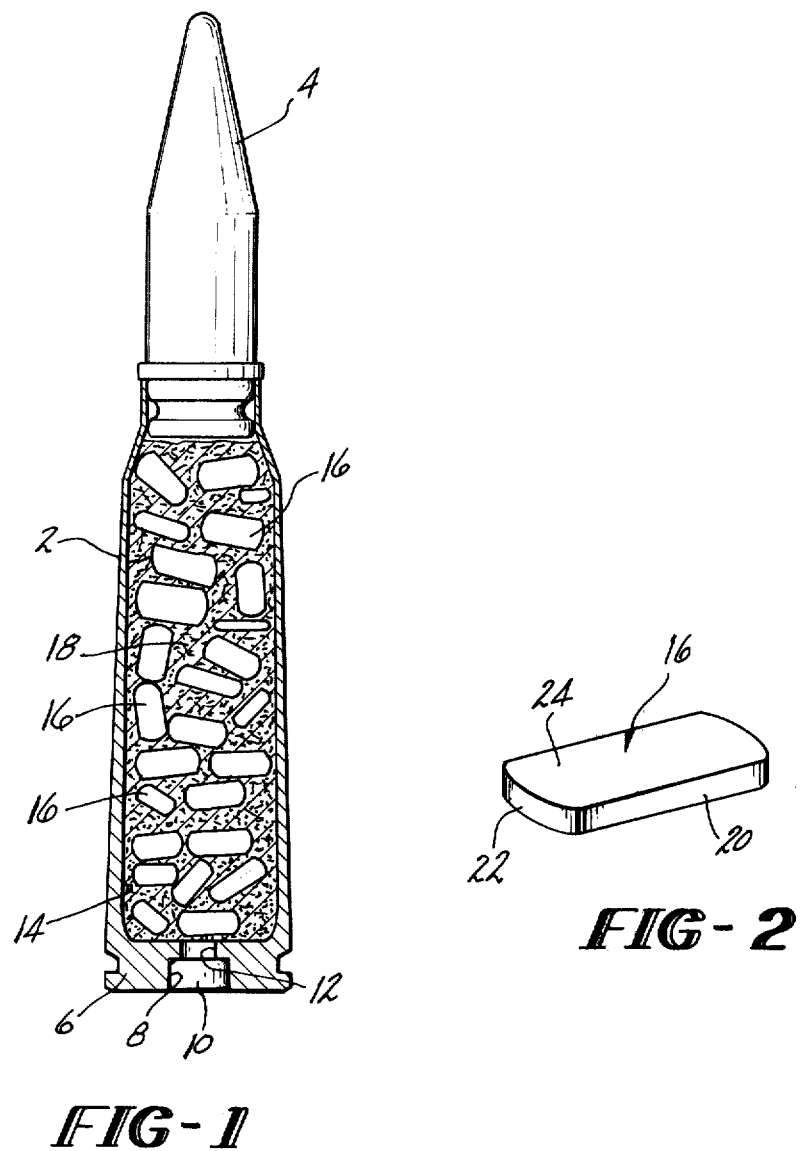
FIG. 1 is a vertical sectional view of a cartridge loaded with the mixed propellant charge of this invention.
FIG. 2 is a perspective view of one of the molded slugs of propellant.

Referring now to FIGS. 1 and 2, the cartridge includes a casing 2 to which a projectile 4 is secured. The basal end wall 6 of the casing 2 is provided with a primer recess 8 in which a conventional primer cap 10 is positioned. A flash hole 12 extends from the primer recess 8 into the interior propellant chamber 14 of the casing 2. The propellant which is packed into the propellant chamber 14 includes a plurality of molded high density slugs 16 of compacted smokeless powder which are relatively homogeneously dispersed throughout a matrix of loose granular smokeless powder 18. The slugs 16 are in the form of small platelets having flat side walls 20, rounded end walls 22, and flat top and bottom walls 24. While the slugs 16 are illustrated in the flat platelet geometric form, it will be understood that the slugs can be made in other geometric shapes without departing from the spirit of the invention.

Figure 3:
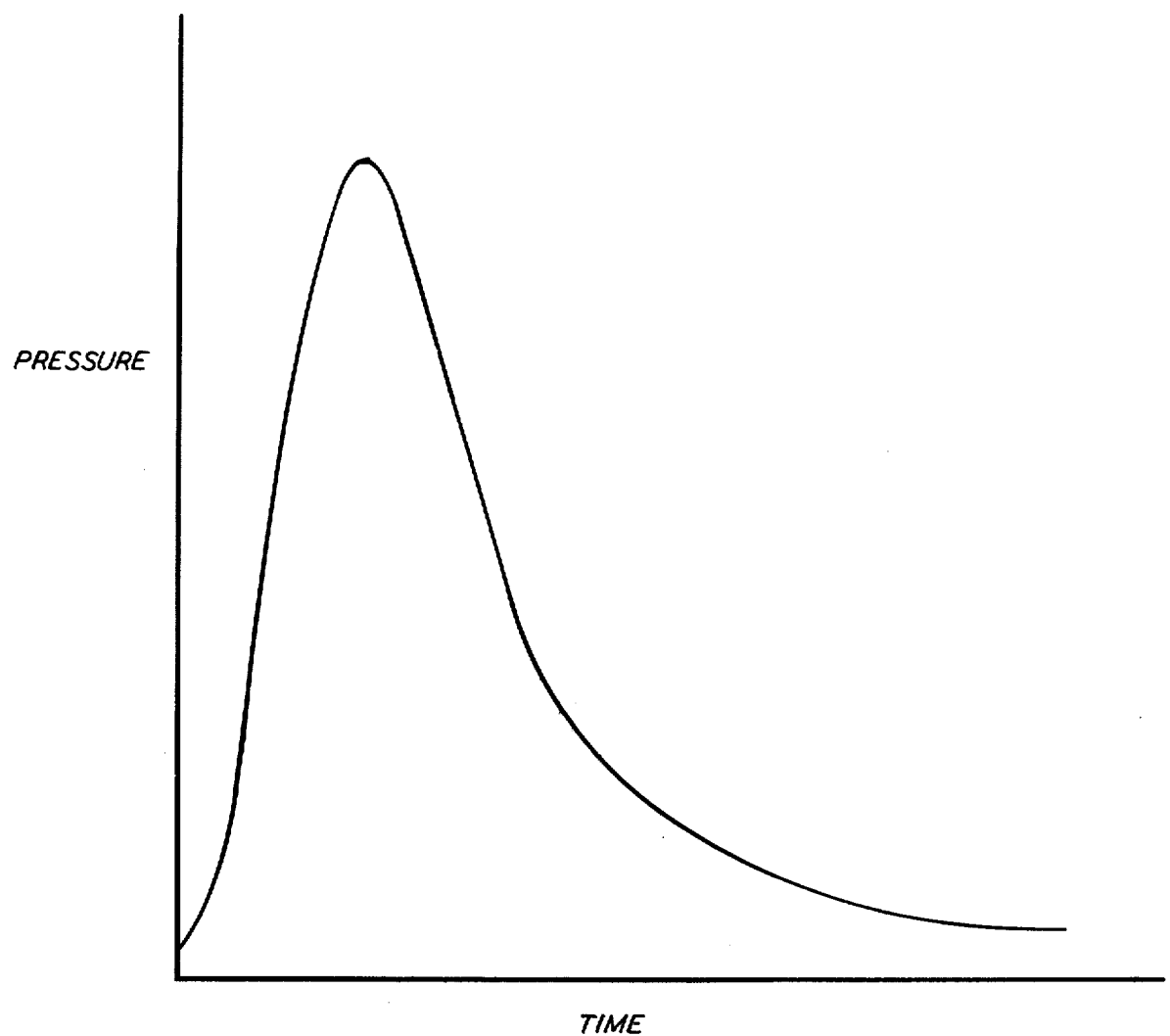
FIG. 3 is a plot of a representative pressure-time function produced by burning a conventional granular propellant charge.

Referring now to FIG. 3, there is shown a characteristic plot of a pressure-time curve produced by burning a conventional granular smokeless powder propellant. As previously noted, peak pressure can be increased by burning a larger amount of propellant, and the time point where peak pressure is reached can be delayed by burning slower burning propellants. In each case, however, the general form of the curve remains the same, e.g. as shown in FIG. 3.

Figure 4:
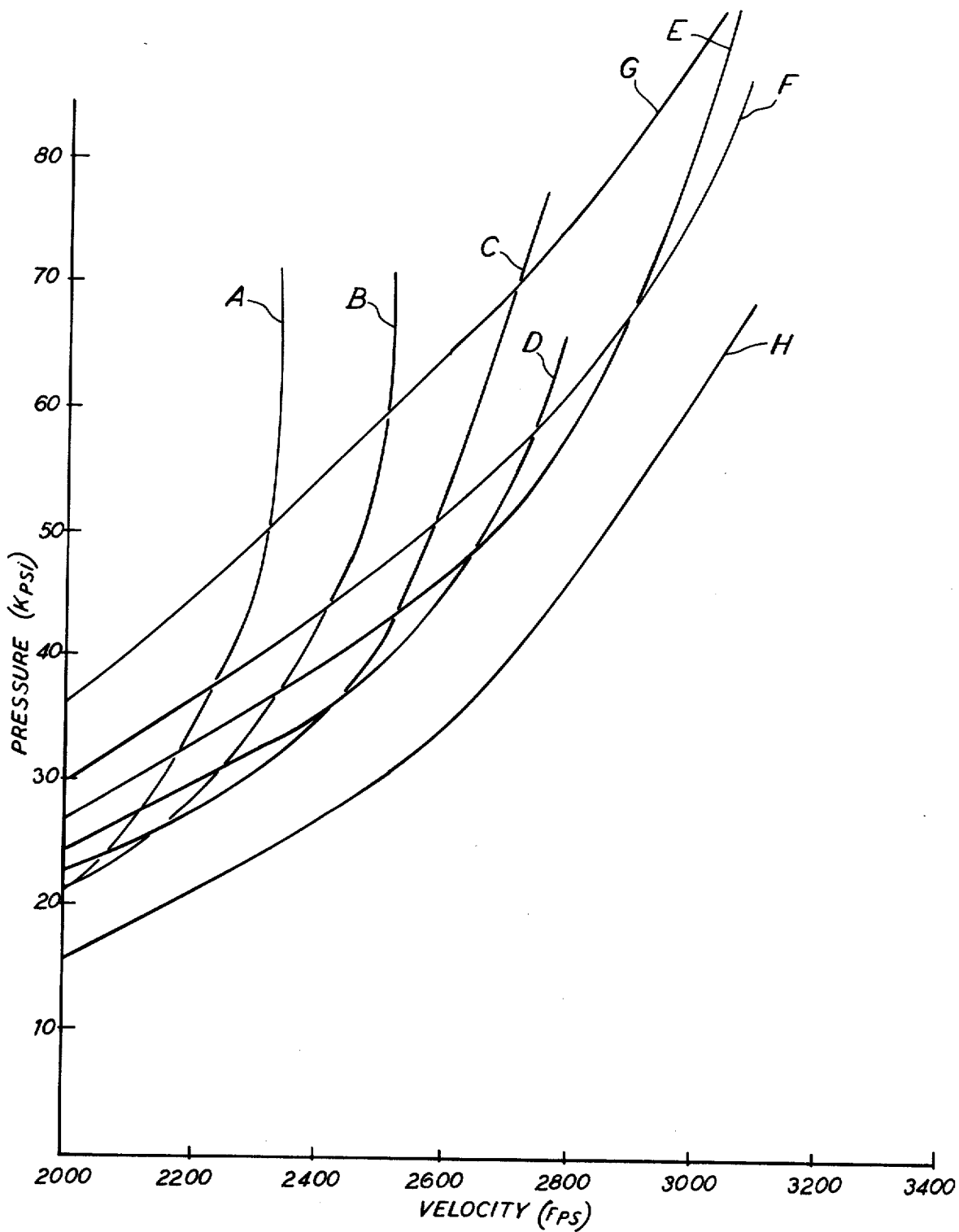
FIG. 4 is a graph showing pressure-velocity performance of conventional granular propellant charges as compared to the pressure-velocity performance of the mixed propellant charge of this invention.

Referring now to FIG. 4, there are shown plots of the pressure-velocity performance of conventional granular charges of smokeless powder having various burning rates. The curves A-G are calculated for a neutral burning pure nitrocellulose propellant in the granular form fired in a 30 mm WECOM system having no bore resistance and utilizing a 3,000 grain projectile. Curves A-G in FIG. 4 represent the performance of progressively slower burning all granular charges of conventional smokeless powders, and curve H represents the performance of a mixed propellant charge formed in accordance with this invention. Curve H is calculated from actual firings with a 30 mm WECOM system having two inches of no bore resistance and a 3,000 grain projectile.

Specifically, curve A represents the performance of a 338 grain charge (0.5 gm./cc. loading density) of a fast burning powder. It will be noted that this powder produces a quick rise in pressure without providing particularly high projectile velocities. A projectile velocity of about 2340 is achieved at an undesirably-high chamber pressure of 70,000 psi. It is noted that an increase in the weight of the propellant charge used would merely increase the chamber pressure without significantly increasing the projectile velocity. Assuming that desirable chamber pressures are in the 30,000 to 40,000 psi range for this system, this propellant would only achieve projectile velocities of about 2160 fps to 2260 fps.

Curve B represents the performance of a slower burning granular powder charge of 405 grains (.6 gm./cc. loading density). It will be noted that this powder, in the 30,000 to 40,000 psi range will produce projectile velocities of about 2220 fps to about 2380 fps.

Curve C represents the performance of a slower burning granular powder charge of 473 grains (0.7 gm./cc. loading density). This powder, in the 30,000 to 40,000 psi range produces projectile velocities of about 2280 fps to about 2480 fps.

Curve D represents the performance of a slower burning granular powder charge of 540 grains (0.8 gm./cc. loading density). This powder, in the 30,000 to 40,000 psi range produces projectile velocities of about 2200 fps to about 2510 fps.

Curve E represents the performance of a slower burning granular powder charge of 608 grains (0.9 gm./cc. loading density). This powder, in the 30,000 to 40,000 psi range produces a projectile velocity of about 2100 fps to about 2420 fps.

Curve F represents the performance of a slower burning granular powder charge of 675 grains (1.0 gm./cc. loading density). This powder, in the 30,000 to 40,000 psi range produces a projectile velocity of about 2000 fps to about 2300 fps.

Curve G represents the theoretical performance of a slower burning granular powder charge of 775 grains (1.1476 gm./cc. loading density). This theoretical charge weight was chosen because it equals a charge weight made possible by the use of the mixed propellant of this invention. This propellant only produced a projectile velocity of 2080 fps at 40,000 psi chamber pressure.

Curve H represents the performance of the mixed propellant charge of this invention which has a burning rate that is about equal to the burning rate of the propellant of Curve C. The mixed propellant charge of Curve H contained 775 grains (1.1476 gms./cc. loading density) of which 400 grains were in the form of compacted molded high density slugs, and 375 grains were in the granular form. The mixed propellant charge in the 30,000 to 40,000 psi range produced projectile velocities of about 2500 fps to about 2700 fps. Thus it will be noted that the mixed propellant charge of this invention will produce a higher projectile velocity at any given pressure than will the purely granular propellant charges of the prior art at the same pressure. Furthermore, the higher projectile velocity will be produced without a dangerously high increase in chamber pressure.

Testing has demonstrated that projectile velocity can be increased while at the same time lowering chamber pressure by selecting for the molded slugs a geometrical form which provides an increased surface area to weight ratio. One such geometrical form which has been demonstrated as accomplishing this result is a cylindrical slug having end walls provided with conical depressions.

The mixed propellant charge of this invention can be composed of a mixture of compacted slugs of smokeless powder propellant dispersed throughout a matrix of granular smokeless powder propellant, wherein the propellants forming the slugs and matrix are either the same or different propellants. The slugs may be coated completely or partially with a deterrent, or may be uncoated. The slugs may be made in a great variety of different geometrical shapes. The granular matrix may be deterrent-coated or uncoated.

Those skilled in the art will readily appreciate that the use of a mixed propellant charge having a granular smokeless powder component and a compacted smokeless powder component will provide a given gun-ammunition system with an increased projectile velocity due to the increased cross-sectional bulk density of the mixed propellant charge as compared to a purely granular propellant charge. Also the use of a mixed propellant charge permits the system to be varied by several new parameters for further tailoring of the system's performance. The two components may or may not be made of the same base propellant, and may or may not display the same ballistic characteristic. The two components may or may not be wholly or partially coated with combustion varying deterrents. The ignition of the molded component probably occurs at some time interval after ignition of the granular component, it apparently requiring more energy to ignite the molded slugs than is required to ignite the granular propellant, but once ignited, the molded slugs surprisingly burn in substantially the same manner as if they were in granular form.

Since many changes and variations of the disclosed embodiment of the invention may be made without departing from the inventive concept, it is not intended to limit the invention otherwise than as required by the appended claims.

What is claimed is:

1. A propellant charge for use in a cartridge, said propellant charge comprising a first constituent of compacted nitrocellulose base smokeless powder and a second constituent of loose granular nitrocellulose base smokeless powder, said propellant charge having a maximum packing density which is greater than about 1.0 gm/cc.

2. A propellant charge for use in a cartridge, said propellant charge comprising a plurality of compacted bodies of nitrocellulose base smokeless powder dispersed in a matrix of loose granular nitrocellulose base smokeless powder, said propellant charge having a maximum packing density which is greater than about 1.0 gm/cc.

3. A propellant charge for use in a cartridge, said propellant charge comprising a plurality of compacted bodies of nitrocellulose base smokeless powder substantially homogeneously dispersed throughout a matrix of loose granular nitrocellulose base smokeless powder to form a mixture having a maximum packing density which is greater than about 1.0 gm/cc.

4. The propellant charge of claim 3, wherein the maximum packing density of said mixture is in the range of greater than about 1.0 gm/cc. to less than about 1.4 gm/cc.

5. A cartridge comprising a casing, a projectile in said casing, a primer, and a propellant charge disposed in a chamber within said casing, said propellant charge including a first portion of compacted nitrocellulose base smokeless powder and a second portion of loose granular nitrocellulose base smokeless powder, said propellant charge having a maximum packing density within said casing chamber which is greater than about 1.0 gm/cc.

6. A cartridge comprising a casing, a projectile secured to said casing, a propellant chamber in said casing adjacent said projectile, and a propellant charge within said propellant chamber, said propellant charge including a plurality of compacted bodies of nitrocellulose base smokeless powder dispersed in a matrix of loose granular nitrocellulose base smokeless powder, and said propellant charge having a maximum packing density which is greater than about 1.0 gm/cc.

7. A cartridge comprising a casing, a projectile secured to said casing, a propellant chamber in said casing, and a propellant charge in said propellant chamber, said propellant charge comprising a plurality of molded bodies of nitrocellulose base smokeless powder substantially evenly dispersed throughout a matrix of loose granular nitrocellulose base smokeless powder, said propellant charge having a maximum packing density of greater than about 1.0 gm/cc.

8. The cartridge of claim 7, wherein said propellant charge has a maximum packing density in the range of greater than about 1.0 gm/cc. to less than about 1.4 gm/cc.

* * * * *

UNITED STATES PATENT OFFICE
CERTIFICATE OF CORRECTION

Patent No. 3,938,440              Dated February 17, 1976

Inventor(s) Dooley & Cook

It is certified that error appears in the above-identified patent and that said Letters Patent are hereby corrected as shown below:

Col. 1, line 25, please delete "nigher" and insert --higher--;

Signed and Sealed this eighth Day of June 1976

[SEAL]

Attest:

RUTH C. MASON
*Attesting Officer*

C. MARSHALL DANN
*Commissioner of Patents and Trademarks*